(12) United States Patent
Nakamura et al.

(10) Patent No.: US 6,613,537 B2
(45) Date of Patent: Sep. 2, 2003

(54) PYRROLOPYRIDINIUM DERIVATIVES

(75) Inventors: Ko Nakamura, Hyogo (JP); Seikoh Horiuchi, Kumamoto (JP); Norie Araki, Kumamoto (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/795,342

(22) Filed: Feb. 28, 2001

(65) Prior Publication Data

US 2002/0028464 A1 Mar. 7, 2002

(30) Foreign Application Priority Data

Feb. 29, 2000 (JP) ........................................ 2000-054245

(51) Int. Cl.$^7$ ...................... G01N 33/543; C07K 16/18; C07D 491/22; C07D 471/02
(52) U.S. Cl. ...................... 435/7.92; 424/92; 436/171; 436/172; 436/501; 436/503; 436/811; 436/815; 530/388.25; 530/388.9; 530/389.3; 530/389.8; 546/83; 546/113
(58) Field of Search .................. 530/388.9, 388.25, 530/389.3, 389.8; 546/83, 113; 436/501, 503, 811, 815, 172, 171; 424/9.2; 435/7.92

(56) References Cited

U.S. PATENT DOCUMENTS

| 5,338,850 A | 8/1994 | Nakamura et al. |
| 5,686,251 A | 11/1997 | Horiuchi et al. |

FOREIGN PATENT DOCUMENTS

| EP | 0 288 256 A2 | 10/1988 |
| EP | 0 360 258 A2 | 3/1990 |
| EP | 0695750 | 7/1996 |
| JP | 06/73057 | 3/1994 |
| JP | 08/48686 | 2/1996 |
| JP | 10-158265 | 6/1998 |
| WO | WO 89/04491 | 5/1989 |
| WO | WO 91/02978 | 3/1991 |

OTHER PUBLICATIONS

Simizu et al, Chem. Abstract No. 1999: 681355 (1999).*
Sensi, et al., "Advanced Nonenzymatic Glycation Endproducts (Age): Their Relevance To Aging And The Pathogenesis Of Late Diabetic Complications", *Diabetes Research*, (1991) 16, 1–9.
Brownlee, M., "Glycation Products and the Pathogenesis of Diabetic Complications", *Diabetes Care*, vol. 15, No. 12, Dec. 1992, pps. 1835–1843.
Brownlee, et al., "Advanced Glycosylation End Products In Tissue And The Biochemical Basis Of Diabetic Complications", *The New England Journal of Medicine*, vol. 318, No. 20, 1315–1321.
Lyons, "Glycation and Oxidation: A Role in the Pathogenesis of Atherosclerosis", *The American Journal of Cardiology*, vol. 71, Feb. 25, 1993, pps. 26B–31B.
Harrington, et al., "A glycation connection", *Nature*, vol. 370, Jul. 28, 1994, pps. 247–248.
Yan, et al., "Non–enzymatically glycated tau in Alzheimer's disease induces neuronal oxidant stress resulting in cytokine gene expression and release of amyloid β–peptide", *Nature Medicine*, vol. 1, No. 7, Jul. 1995, pps. 693–699.
Lamb, et al., "Serum Glycated Albumin and Fructosamine in Renal Dialysis Patients", *Nephron*, 1993; 64:82–88.
Lamb, et al., "Glycated albumin in serum and dialysate of patients continuous ambulatory peritoneal dialysis", *Clinical Science* (1993) 84, 619–626.
Huber, et al., "Formation of 2–(2–furoyl)–4(5)–(2–furyl)–1H–imidazole in the Maillard Reaction", *Carbohydrate Research*, vol. 182, No. 2, pps. 301–306.
Nakamura, et al., "Crosslines A and B as Candidates for the Fluorophores in AGE– and Diabetes–related Cross–linked Proteins, and their Diacetates produced by Maillard Reaction of α–N–Acetyl–L–lysine with o–Glucose", *J. Chem. Soc. Chem. Commun.*, 1992, pps. 992–994.
Horiuchi et al., "AGE (glycation) and Diseases," *BIO Clinica*, 11(5), p. 314 (1996) (Japanese).
Morisaki et al., "AGE and Diabetic Complications," *Saishin Igaku*, 49, 2, p. 248 (1994) (Japanese).

* cited by examiner

*Primary Examiner*—Mary E. Ceperley
(74) *Attorney, Agent, or Firm*—Hollander Law Firm, P.L.C.

(57) ABSTRACT

The present invention is drawn to pyrrolopyridinium derivatives having a new structural skeleton, preferably containing an intramolecular hemiacetal, which is clearly different from any known Advanced Glycation Endproduct (AGE) and which, when present in an organism, has a bioactivity unlike the conventional AGE. The present invention provides pyrrolopyridinium derivatives and pharmaceutically acceptable salts thereof, an antibody prepared from said derivatives as a hapten, a method for the diagnosis of diabetes, diabetic complications, renal failure, dialysis-related complications, amyloidosis, aging, diseases accompanied by aging, etc. using said derivatives or an antibody prepared therefrom and a method for evaluating effectiveness of pharmaceuticals used to treat diabetes, diabetes-related diseases, dialysis-related complications, aging, diseases accompanied by aging, etc.

21 Claims, No Drawings

PYRROLOPYRIDINIUM DERIVATIVES

FIELD OF THE INVENTION

The present invention relates to novel pyrrolopyridinium derivatives; an antibody prepared from said derivatives as a hapten; a method for the diagnosis of diseases including diabetes, diabetic complications, amyoidosis, renal failure, dialysis-related complications, aging, and diseases accompanied by aging, such as Alzheimer's disease, etc. by measuring said derivative or by measuring reactivity in the subject with an antibody prepared therefrom; and a method for evaluating the effectiveness of pharmaceuticals which are effective for treating diabetes, diabetic complications, amyloidosis, renal failure, dialysis-related complications, aging, and diseases accompanied by aging, such as Alzheimer's disease, etc.

BACKGROUND OF THE INVENTION

In 1968, glycosylhemoglobin (HbAlc), which is one of the minor components of hemoglobin was identified in vivo and was found to increase in patients diagnosed as having diabetes. With this discovery, the Maillard reaction was shown to occur with proteins in vivo. Despite having been studied mainly in the field of food chemicals, the biological and medical meaning of the Maillard reaction would now receive greatly increased public attention.

The Maillard reaction may be classified into a former stage and a latter stage. In the former stage, a Schiff base is formed by the condensation of an amino group of a protein with an aldehyde group of a reducing sugar and is stabilized as a result of the Amadori rearrangement. In the latter stage, the rearranged Schiff Base is transferred, after a long series of reactions, to an Advanced Glycation Endproduct (AGE). The latter stage end products are characterized by fluorescence, a color change to brown and molecular crosslinking. In recent years, several studies on AGE have investigated the relationship between various diseases and AGE, which is produced particularly in the advanced stages of various diseases.

Several studies have uncovered the participation of AGE in various diseases and in the aging process. See "AGE (glycation) and Diseases" (BIO Clinica, 11(5), p. 314 (1996)), which is a review by Dr. Horiuchi et al. For example, aging is thought to be a process in which various proteins and DNA in tissues are modified or changed until they can no longer be decomposed and removed. The protein and DNA so-modified are accumulated in the body, resulting in a loss of their function. The advanced glycation of tissue proteins is exemplified as one of the causes thereof. In fact, it has been shown that the fluorescence of the hydrolyzed products of skin collagen and lens protein increases with aging and that an excessive advanced glycation of lens proteins participates in the onset of cataracts. In addition, AGE is now being recognized as one of the causes of the aging phenomenon because advanced glycation causes an inhibition of enzymatic activity and a corresponding decrease in the body's ability to decompose intracellular protein. AGE also causes a substance transport disorder brought on by advancedly glycated cytoskeleton protein and DNA mutation caused by a cross-linkage formed between DNA and protein by AGE.

Studies using an antibody to the above-mentioned AGE have uncovered the participation of AGE in various diseases. Still other reports show that an anti-AGE antibody reacts in a concentration-dependent manner with the water-soluble fraction and the alkali-soluble fraction of the normal human lens crystallin, while a very high correlation is observed between anti-AGE antibody reactivity and the aging process; that advanced glycation in the Descemet membrane and lens vesicle of cattle increases with age, as shown by immune electric microscopy; and that the AGE immunoreaction with the petrosal nerve cell correlates with aging, as shown by an immunohistochemical investigation using an antibody.

Fluorescence, which is characteristic of the presence of AGE, is used as an indicator for investigating the correlation between AGE and various diseases. It is known that in diabetic patients fluorescence is significantly higher than it is in healthy people. Moreover, the accumulation of AGE was reported in renal tissues, such as the renal mesangium region, blood vessel walls and urinary tubules, and in the coronary arteriosclerotic nest of diabetic patients. It was also reported that, as a result of immune staining using an anti-AGE antibody, AGE shows almost the same distribution in the peripheral nerves of both experimental diabetic rats and human diabetics. Accordingly, it has been recognized that there is a correlation between diabetes mellitus and AGE.

It has also been shown that an excessive formation of AGE in an organism is a cause of diabetic complications. For example, an advanced glycation of crystallin, which is a lens protein, is one of the causes of diabetic cataracts. It has also been shown that AGE is deeply related to diabetic nephropathy. The glomerular basement membrane in the kidney, comprised of collagen, is advancedly glycated by hyperglycemia and is apt to be bound to albumin, immunoglobulin, and low-density lipoprotein, etc., whereby the basement membrane thickens, thus disturbing the renal filtration function. In addition, reports suggest that AGE may accumulate in mesangium cells and that it may participate in inflammation, such as the secretion of cytokines mediated by a receptor. Recently, it has been reported that a suppressor for the production of AGE is useful in treating diabetic nephropathy. It has been also reported that the myelin protein of a nerve cell is advancedly glycated, suggesting that AGE participates in diabetic neuropathy as well. From these reports, a clear correlation emerges between increased amounts of AGE in the body and the onset of diabetic complications such as diabetic nephropathy, arteriosclerosis, neurosis, retinopathy, cataracts, etc. AGE and diabetic complications are summarized, for example, in a review entitled "AGE and Diabetic Complications" (Saishin Igaku, 49, 2, p. 248 (1994)) by Morisaki, et al.

In addition, a relation between AGE and dialysis-related amyloidosis has been found because fluorescence increases in the protein found in the sera of dialyzed patients. A similar accumulation of AGE occurs at the site where a sediment forms in the amyloid of the carpal tunnel of dialyzed patients.

A recent report suggests that a scavenger receptor recognizing the AGE protein is present in monocytes, macrophages, mesangium cells and endothelial cells, and that the AGE recognition mediated by such a receptor results in the release of cytokine, the promotion of blood vessel permeability, abnormal blood flow, etc. A relationship thus emerges between AGE and the symptoms of inflammation, capillary obstruction, arteriosclerosis, etc. Furthermore, it is suspected that AGE participates in the onset and progress of Alzheimer's disease because AGE is strongly detected in senile plaque, and in amyloid and neurofibril changes which are characteristically noted in the brains of patients suffering from Alzheimer disease.

The Maillard reaction may also generate free radical oxygen. Free radical or active oxygen is receiving much recent public attention as a cause of aging, tissue disorders resulting from diabetes mellitus and the generation of pathological changes resulting from Alzheimer's disease. It is becoming clear that the Amadori compound produced by the initial-stage reaction of the Maillard reaction is oxidized by active oxygen to produce AGE, while at the same time causing the generation of active oxygen. It has been also reported in neuromatous cell strains (SK—N—SH) that neurofibril (PHF) tau-protein generates active oxygen by glycation and that it activates the transcription factor NF—κB. It has also been suggested that an extinction enzyme for active oxygen such as Cu—Zn-superoxide dismutase (Cu—Zn-SOD) is advancedly glycated as its activity lowers with aging. Such glycation of Cu—Zn-SOD becomes over time an essential cause for an increase in oxidative stress and suggests again the relation between Alzheimer's disease and AGE.

Until now, several AGEs such as $N^\epsilon$-carboxymethyllysine (CML), pentosidine, pyralin, $N^\epsilon$-carboxyethyllysine (CEL), glyoxallysine dimer (GOLD) and methylglyoxallysine dimer (MOLD) have been reported.

Antibodies to some of the commercially available AGE compounds have been manufactured and studied. An antibody recognizing such an AGE, 6D12 (Kumamoto Antibody Laboratory) which is an anti-CML monoclonal antibody, has been put on the market. Immunohistological and immunochemical studies, such as the measurement of AGE amounts and immunological staining in human plasma, human serum, human urine, arteriosclerotic tissue, the renal tissue of patients suffering from diabetic nephropathy, the eye tissue of aged people, the cerebral tissue of patients suffering from Alzheimer's disease, etc., using antibodies of the above-mentioned AGEs have been carried out and studies of their medical significance of existence have been conducted.

However, the fact that a large number of biological Maillard reactions and commercial methods exist which produce AGE suggests that various kinds and types of AGE are produced depending upon each situation and that the distribution of AGE in any tissues will vary widely. It is thus desirable to persons skilled in the art to obtain many AGEs having various different properties for the purpose of finding an optimum AGE suitable for each of the various kinds and types of situations in an organism. For example, the present inventors and their co-workers found a pyridinium derivative called Crossline™ (Japanese Patent Laid-Open Hei-06/73057), naphthylidinium derivatives disclosed in Japanese Patent Laid-Open Hei-08/48686 and corresponding U.S. Pat. No. 5,686,251, and pyrrolonaphthylidium derivatives disclosed in Japanese Patent Laid-Open Hei-10/158265, etc. as novel AGEs. U.S. Pat. No. 5,338,850 to Nakamura, et al and corresponding Japanese Laid Open Hei-06/73057 and corresponding European Patent Publication No. 0695750 disclose pyridinium derivatives which are effective in diagnosis of diabetes, diabetic complications, aging, and diseases accompanied by aging. An antibody prepared from the pyridinium derivatives as a hapten is also disclosed. Evaluation of the effectiveness of pharmaceuticals for the treatment of these ailments is also described. Nevertheless, there remains a demand for a novel AGE produced under a situation that is different from the conventional one or, in other words, for a novel AGE having a structural skeleton different from the conventional AGE.

The present inventors have conducted continued studies on crosslinked substances which are produced by each of the processes of nonenzymatic glycation and the oxidation of proteins for use as an indicator to diagnose diabetic complications, dialysis complications and aging. As a result thereof, they have found novel and unobvious pyrrolopyridinium derivatives which have a completely new structural skeleton from that of known AGEs.

SUMMARY OF THE INVENTION

The present invention provides: (a) novel pyrrolopyridinium derivatives and salts thereof; (b) an antibody prepared from said derivatives as a hapten; (c) a method for the diagnosis of diabetes, diabetic complications, dialysis-related complications, amyloidosis, aging, diseases accompanied by aging, etc. using said derivatives or an antigen or antibody thereof; and (d) a method for evaluating effectiveness of pharmaceuticals used to treat diabetes, diabetes-related diseases, dialysis-related complications, aging, diseases accompanied by aging, etc.

The novel pyrrolopyridinium derivatives of the present invention are represented by the following formulae (I), (II) or (III), and steroisomers and enantiomers thereof and pharmaceutically acceptable salts of the derivatives, stereoisomers and enantiomers:

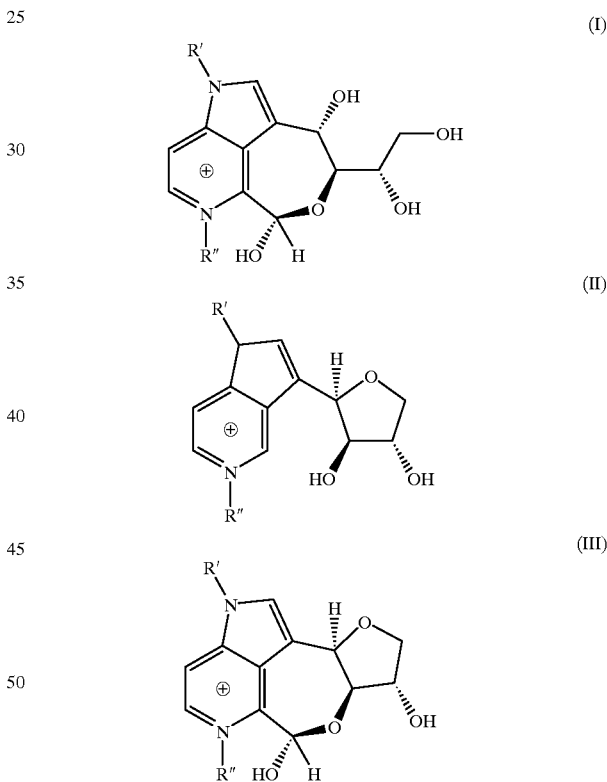

wherein each of R' and R" is, independently, an alkyl group which may have an amino, a protected amino and/or a carboxyl substituent.

A method of manufacturing the pyrrolopyridinium derivatives of the present invention may comprise, for example, reacting a compound of the formula R'NH$_2$ or R"NH$_2$, wherein R' and R" are the same groups as mentioned above, with sugars, for example, hexose such as glucose, fructose, galactose, mannose or deoxyglucose, amino sugar such as glucosamine or galactosamine, oligosaccharide such as saccharose, for a sufficient period of time to give the derivatives of the present invention, followed by recovering the derivatives from the reaction mixture. The pyrrolopyridinium derivatives of the present invention can also be manufactured by hydrolyzing the product obtained by reacting a sugar, as defined above, with protein or peptide as amine component.

DETAILED DESCRIPTION OF THE INVENTION

The novel pyrrolopyridinium derivatives of the present invention are represented by the following formulae (I), (II) or (III), stereoisomers and enantiomers thereof, and pharmaceutically acceptable salts of the derivatives of formulae (I), (II), or (III), stereoisomers and enantiomers thereof:

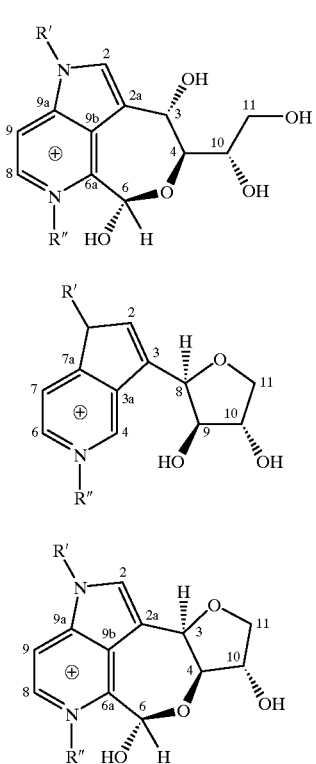

wherein R' and R" is the same or different and each of them is an alkyl group which may have an amino, a protected amino and/or a carboxyl substituent.

Examples of the preferred alkyl for R' and R" in the above general formula, (I), (II) and (III) are linear or branched alkyl having 1 to 6 carbon atom(s) such as methyl, ethyl, propyl, isopropyl, butyl, isobutyl, sec-butyl, tert-butyl, pentyl, isopentyl, neopentyl, tert-pentyl, hexyl and dimethylbutyl.

The alkyl groups R' and R" may be substituted with at least one protected amino group. Protective groups for the amino substituent on R' or R" include, for example, those which are commonly used in the field of peptide synthesis. These may include, for example, formyl, acetyl, tosyl, benzyloxycarbonyl, p-methoxybenzyloxycarbonyl, p-chlorobenzyloxycarbonyl, p-nitrobenzyloxycarbonyl, p-phenylazobenzyloxycarbonyl, p-methoxyphenylazobenzyloxycarbonyl, tert-butoxycarbonyl (Boc), p-toluenesulfonyl (Tos), tert-amyloxycarbonyl, p-biphenylisopropyloxycarbonyl and diisopropylmethyloxycarbonyl groups.

Among the pyrrolopyridinium derivatives of the present invention represented by general formulae (I), (II) and (III), pyrrolopyridinium derivatives wherein R' and R" are alkyl having amino and/or carboxyl groups can easily be combined with a carrier protein as haptens useful, in particular, for preparation of the antibody of the present invention. The carrier for combining with a hapten for the preparation of an antibody of the present invention, may include commonly-used carriers such as protein (e.g. serum albumin, keyhole lympet hemocyanin) and polymers (e.g. polylysine).

The pyrrolopyridinium derivatives of the present invention include salts of the derivatives represented by general formulae (I), (II) and (III). These salts may include pharmaceutically acceptable salts with at least one metal, acid or base. Exemplary salts may include salts with acids like hydrochloric acid, sulfuric acid, nitric acid, hydrobromic acid, phosphoric acid, perhydrochloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphtalenesulfonic acid and sulfanilic acid. Further examples may include addition salts with ammonia or with organic bases such as organic amines; and salts with an alkali metal such as sodium and potassium; salts with an alkali earth metal such as magnesium, calcium and barium; and salts with other metals such as aluminum and zinc.

The salts of the pyrrolopyridinium derivatives of the present invention may be manufactured by conventional methods from the pyrrolopyridinium derivatives of the present invention in a free form and may include mixed salts. Likewise, salts of the pyrrolopyridinium derivatives of the present invention may be readily converted from salt form to a free form by conventional methods.

If the pyrrolopyridinium derivatives of the present invention have stereoisomers such as cis-trans isomers, optical isomers, conformational isomers, or if there are hydrates and/or complexes of the pyrrolopyridinium derivatives of the present invention, the pyrrolopyridinium derivatives of the present invention include any and all of them.

A method of manufacturing the pyrrolopyridinium derivatives of the present invention may comprise, for example, reacting a compound of the formula R'NH$_2$ or R"NH$_2$, wherein R' and R" are the same groups as mentioned above, with sugars, for example, hexose such as glucose, fructose, galactose, mannose or deoxyglucose, amino sugar such as glucosamine or galactosamine, oligosaccharide such as saccharose, for a sufficient period of time to give the derivatives of the present invention, followed by recovering the derivatives from the reaction mixture. The pyrrolopyridinium derivatives of the present invention can also be manufactured by hydrolyzing the product obtained by reacting a sugar, as defined above, with protein or peptide as amine component.

There is no particular restriction on the reaction conditions such as reaction temperature, reaction time, pH, etc. and they may be readily established. For example, an easy procedure comprises allowing the reaction mixture to stand at room temperature and at atmospheric pressure, however, the reaction can be accelerated by heating and the like.

The pyrrolopyridinium derivatives of the present invention prepared as described above may be purified, for example, by conventional means such as distillation, chromatography, recrystallization, etc. The pyrrolopyridinium derivatives of the present invention may be readily identified by conventional means such as NMR, mass analysis, fluorescence spectroscopy, etc.

In manufacturing an antibody of the pyrrolopyridinium derivatives of the present invention, a derivative of the present invention is polymerized with a carrier, for example, bovine serum albumin (BSA) or limpet blood dye protein (KLH), using a conventional method to make a hapten, for example a method such as that used to make an antibody to pentosidine as described in the article (Clin. Chem., 40/9, 1766–1773 (1994)). The product hapten is then used in a conventional immunization method, such as immunizing a mouse, rabbit, or the like. Following the immunizing step, a polyclonal antibody or a monoclonal antibody of the pyrrolopyridinium derivative of the present invention can be prepared by conventional methods.

The pyrrolopyridinium derivatives of the present invention can be measured via a conventional method such as ELISA or immunological staining using an antibody prepared from a derivative. The pyrrolopyridinium derivatives of the present invention can be also measured directly by chromatography, such as HPLC or the like, or by spectroscopy, for example, utilizing their fluorescent wave length.

The amount of the pyrrolopyridinium derivatives of the present invention and antibodies prepared therefrom can be measured and used as an index for the degree of accumulation of Advanced Glycation Endproducts in vivo, whereby the progress of diabetes mellitus, diabetic complications, renal failure, dialysis-related complications, amyloidosis, aging or diseases accompanied by aging can be evaluated. Also, the produced amount and the accumulated amount of the pyrrolopyridinium derivatives of the present invention and antibodies prepared therefrom can be measured in the presence and absence of a test drug to evaluate the pharmaceutical effectiveness of a test drug used to treat diabetes mellitus, diabetic complications, dialysis-related complications, amyloidosis, aging or diseases accompanied by aging.

Substrates to be measured for the pyrrolopyridinium derivatives of the present invention and antibodies prepared therefrom include, for example, living tissues, living tissue extracts, body fluid and/or urine; preferable examples of substrates may include human skin tissues, human skin tissue extracts, human lens extracts, human arteriosclerotic tissues, renal tissues of patients suffering from diabetic nephropathy, tissues of aged people, cerebral tissues of patients suffering from Alzheimer disease, human blood, human plasma, human serum and human urine; and, particularly preferable examples of such substrates may include, human skin tissues, human skin tissue extracts, human plasma, human serum and human urine.

Preferred embodiments of the present invention are as follows.

(1) Pyrrolopyridinium derivatives represented by the above-mentioned formulae (I), (II) or (III) and pharmaceutically acceptable salts thereof.
(2) An antibody prepared from the pyrrolopyridinium derivatives according to subparagraph (1) useful as an antibody against Advanced Glycation Endproducts and against the pyrrolopyridinium derivatives of the present invention which are produced in the body.
(3) A method for the diagnosis of diabetes, diabetic complications, dialysis-related complications, amyloidosis, aging and diseases accompanied by aging comprising using the pyrrolopyridinium derivatives according to subparagraph (1) as an indicator.
(4) A method for the diagnosis of diabetes, diabetic complications, dialysis-related complications, amyloidosis, aging and diseases accompanied by aging comprising using the antibody according to subparagraph (2) in an assay as an antibody against Advanced Glycation Endproducts and against the pyrrolopyridinium derivatives of the present invention which are produced in the body.
(5) A method for diagnosis according to subparagraphs (3) or (4) comprising measuring the pyrrolopyridinium derivatives of the present invention in a living tissue, an extract from the living tissue, body fluid and/or urine.
(6) A method for diagnosis according to subparagraph (5) comprising measuring the pyrrolopyridinium derivatives of the present invention in body fluid and/or urine.
(7) A method for diagnosis according to subparagraph (6) wherein an extract from body fluid and/or urine is human blood, human plasma, human serum or human urine.
(8) A method for diagnosis according to subparagraph (5) comprising measuring the pyrrolopyridinium derivatives of the present invention in a living tissue and/or an extract from the living tissue.
(9) A method for diagnosis according to subparagraph (8) wherein an extract from a living tissue and/or an extract from the living tissue is human skin tissues or human skin tissue extracts.
(10) A method for diagnosis comprising measuring the pyrrolopyridinium derivatives of the present invention to evaluate the production and/or the accumulation of Advanced Glycation Endproduct(s) in vivo according to any of subparagraphs (3) to (9).
(11) A method for evaluating of the effectiveness of pharmaceuticals such as therapeutic agents for diabetes, those for diabetic complications, those for dialysis-related complications, those for amyloidosis, preventive agents for aging and therapeutic agents for diseases accompanied by aging comprising using the pyrrolopyridinium derivatives according to subparagraph (1) as an indicator.
(12) A method for evaluating of the effectiveness of pharmaceuticals such as therapeutic agents for diabetes, those for diabetic complications, those for dialysis-related complications, those for amyloidosis, preventive agents for aging and therapeutic agents for diseases accompanied by aging comprising using the antibody according to subparagraph (2) to evaluate the production and/or the accumulation of Advanced Glycation Endproduct(s) in vivo.

The present invention is further illustrated by the following non-limiting examples wherein all parts, percentages and ratios are by weight, all temperatures are in ° C., and all reactions are conducted at about atmospheric pressure and room temperature unless indicated to the contrary:

EXAMPLE 1

Glucose (79.2 g; 400 mM) and 45.3 g (400 mM) of γ-aminobutyric acid were dissolved in 1.1 L of a 250 mM phosphate buffer (pH 7.3) and allowed to stand at 37° C. for 60 days. The reaction solution (330 mL) was acidified (pH: around 2) with trifluoroacetic acid (TFA), without concentrating, and then added to a column of Amberlite XAD-2 (Organo; 57 mm diameter×750 mm) equilibrated with deionized water. This was further eluted with deionized water whereupon each 100 mL was fractionated. The resulting fractions were successively analyzed by an HPLC chromatography and the fractions containing compound 1 were collected, concentrated and evaporated to dryness. The dry product was added to Develosil ODS LOP-45S (Nomura Kagaku) equilibrated with 0.2% TFA and eluted with 7% acetonitrile/0.2% TFA. Each 15 mL of the eluate was collected by a fraction collector, and each fraction was analyzed by a reverse phase HPLC (column: Inertsil ODS-3V; 4.6 mm diameter×250 mm; solvent: 20% methanol/0.2% TFA; flow rate: 0.8 mL/min). The fractions containing compound 1 were collected, concentrated and evaporated to dryness, and then said fractions were repeatedly purified using Develosil ODS LOP-45S (5% acetonitrile/0.2% TFA). Based upon the analytical results obtained by reverse phase HPLC (column: Inertsil ODS-3V; 4.6 mm diameter×250 mm; solvent: 20% methanol/0.2% TFA; flow rate: 0.8 mL/min), the fractions were divided into three groups depending upon the spectral peaks or the components of each group and two of them were further purified (Fr-1: 340 mg; Fr-2: 400 mg). Fr-1 was subjected to a reverse phase HPLC (column: Inertsil ODS-3; 20 mm diameter×250 mm; flow rate: 10.0 mL/min; eluent: 8% acetonitrile/0.2% TFA) and, by detection of a peak in UV absorption at a wavelength of 280 nm, a fraction containing the main component, i.e. compound 1 or (8-(1,2-dihydroxyethyl)-6,9-dihydroxy-2,5-bis(3-carboxypropyl)-2,6,8,9-tetrahydro-7-oxa-2-aza-5-azoniabenzo [cd]azulene), was isolated. The isolate was concentrated in vacuo to a volume of about 5 mL, and was added to Sep-Pak Vac C18 Cartridge equilibrated with deionized water, well washed with deionized water to remove trifluoroacetic acid and eluted with 50% acetonitrile. The washed concentrate was then further concentrated and evaporated to dryness to give compound 1 (95 mg). Fr-2 was subjected to a reverse phase HPLC (column: Inertsil OSD-3: 20 mm diameter×250 mm; flow rate: 8.0 mL/min; eluent: 12% acetonitrile/0.2% TFA) and, by detection of a peak in UV absorption at a wavelength of 280 nm, a fraction containing the main component was isolated. The isolate was concentrated in vocuo to a volume of about 5 mL. The concentrate was then added to Sep-Pak Vac C18 Catridge equilibrated with deionized water, well washed with deionized water to remove trifluoroacetic acid and eluted with 50% acetonitrile. The washed concentrate was further concentrated and evaporated to dryness to givecompound 2, (3-(3,4-dihydroxytetrahydrofuran-2-yl)-1,5-bis(3-carboxypropyl)-1H-pyrrolo[3,2-c]pyridinium) (72 mg).

EXAMPLE 2

Compound 1 (19.6 mg) was dissolved in 3 mL of 2N HCl and stirred at room temperature. The reaction was checked from time to time by means of a reverse phase HPLC (column: Inertsil ODS-3V: 4.6 mm diameter×250 mm; flow rate: 0.8 mL/min; eluent: 12% acetonitrile/0.2% TFA). After 12 hours, the reaction solution was concentrated in vacuo and evaporated to dryness, the residue was purified by a reverse phase HPLC (column: Inertsil ODS-3; 10 mm diameter×250 mm; flow rate: 4.0 mL/min; eluent: 12% acetonitrile/0.2% TFA). Each of the resulting fractions was concentrated in vocuo to a volume of about 5 mL; the concentrate was added to Sep-Pak Vac C18 Cartridge equilibrated with deionized water, well washed with deionized water to remove trifluoroacetic acid and eluted with 50% acetonitrile; and the eluate was concentrated in vacuo and evaporated to dryness to yield a material comprising compound 3, (8-(1,2-dihydroxyethyl)-1,5-bis (3-carboxypropyl)-2,6,8,9-tetrahydro-7-oxa-2-aza-5-azoniabenzo [cd]cyclopenta[h]azulene-6,8-diol) (6.9 mg).

EXAMPLE 3

Glucose (27.0 g; 200 mM) and 28.2 g (200 mM) of $N^\alpha$-acetyllysine were dissolved in 750 mL of a 250 mM phosphate buffer (pH 7.3) and allowed to stand at 37° C. for 56 days. Without concentrating, the reaction solution was acidified (pH: around 2) with trifluoroacetic acid and added to a sulfonate ion-exchange resin (Diaion PK-216; Mitsubishi Chemical). The column was washed with water and eluted with 2N aqueous ammonia. The fraction was concentrated and evaporated to dryness, added to Develosil ODS LOP-45S (Nomura Kagaku) equilibrated with 0.2% TFA and eluted with 10% methanol/0.2% TFA and 20% methanol/0.2% TFA, while successively increasing the methanol concentration. The fraction which was eluted with 20% methanol/0.2% TFA was further purified by an STR ODS-II column (Shimadzu Techno Research) to yield compound 4 and compound 5.

EXAMPLE 4

The same reaction as in Example 3 was carried out using $N^\alpha$-tert-butoxycarbonyl-L-lysine as the amine component and the product was separated/purified, dissolved in TFA and allowed to stand for 30 minutes to remove a tertiary butoxycarbonyl group, whereby compound 6 was prepared.

The physical properties of the resulting compounds of the present invention are shown below. The labeled substances discussed below were manufactured by the same methods as set forth in the above Examples, using glucose wherein the carbon at the 1-position or at all carbon positions was/were labeled with $^{13}C$ and used for the structural analysis. The fluorescent spectrum and the ultraviolet (UV) spectrum were measured by a 650-4 Fluorescence Spectrophotometer (Hitachi) and a DU-650 (Beckman) spectrophotometer, respectively, in methanol. The spattered ion mass analysis spectrum (SIMS) was measured by an M-80B (Hitachi) device using glycerol as a matrix. The nuclear magnetic resonance (NMR) spectrum was measured in heavy water using an ARX-500 (Bruker) device, wherein the proton having a 500.13 MHz resonance frequency and the $^{13}C$ having a 125.77 MHz resonance frequency were calibrated to 0.00 ppm. Assignments of the $^1H$-NMR spectrum and the $^{13}C$-NMR spectrum were determined by a two-dimensional NMR such as $^1H$—$^1H$ COSY, HMQC and HMBC.

Compound 1
Fluorescent spectrum: EXmax=325 nm, EMmax=440 nm
SIMS: m/z 439
NMR spectrum: shown in Table 1

TABLE 1

NMR SPECTRUM for COMPOUND 1

(MeOH-d4)

| C# | $^{13}C$ (ppm) | $^1H$ (ppm) | (Hz) |
|---|---|---|---|
| 3'[a] | 25.2 | * | m |
| 3"[a] | 26.9 | * | m |
| 2'[b] | 30.5 | * | m |
| 2"[b] | 30.6 | * | m |
| 4' | 46.0 | 4.44 | t (7) |
| 4" | 55.4 | 4.55/4.82 | m, m |
| 11a | 63.4 | 3.70 | dd (7, 12) |
| 11b | 63.4 | 3.95 | dd (3, 12) |
| 3 | 65.0 | 5.39 | s |
| 10 | 70.1 | 3.98 | ddd (3, 7, 9) |
| 4 | 72.4 | 4.54 | d (9) |
| 6 | 91.5 | 6.80 | s |
| 9 | 108 | 8.07 | d (7) |
| 2a | 120.5 | | |
| 9b | 121.2 | | |
| 8 | 135.6 | 8.47 | d (7) |
| 2 | 135.8 | 7.97 | s |
| 9a | 142.0 | | |
| 6a | 149.8 | | |
| COOH'[c] | 175.3 | | |
| COOH"[c] | 175.5 | | |

[a]–[c]Assignments with the same C# may be interchanged. For example, 3'[a] and 3"[a] can be interchanged.
*Not assigned

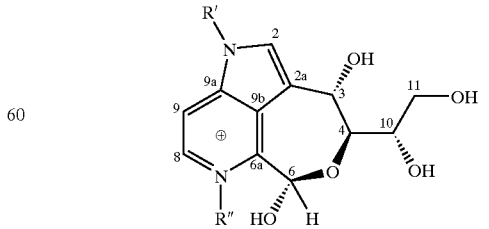

R', R" = CH$_2$(CH$_2$)$_2$COOH

Compound 2
  Fluorescent spectrum: EXmax=331 nm, EMmax=466 nm
  SIMS: m/z 393
  NMR spectrum: shown in Table 2

TABLE 2

NMR SPECTRUM for COMPOUND 2

| C# | $^{13}$C (ppm) | $^{1}$H (ppm) | (Hz) |
|---|---|---|---|
| 3'$^a$ | 25.3 | * | m |
| 3"$^a$ | 26.8 | * | m |
| 2'$^b$ | 30.6 | * | m |
| 2"$^b$ | 30.7 | * | m |
| 4' | 46.0 | 4.42 | t (7) |
| 4" | 59.5 | 4.65 | br.t (7) |
| 10 | 70.9 | 4.32 | ddd (2, 5, 5) |
| 11a | 73.6 | 3.93 | dd (2, 10) |
| 11b | 73.6 | 4.42 | dd (5, 10) |
| 8 | 76.3 | 5.01 | d (8) |
| 9 | 77.5 | 4.11 | dd (5, 8) |
| 7 | 108.3 | 8.07 | d (7) |
| 3 | 119.1 | | |
| 3a | 123.5 | | |
| 2 | 132.3 | 7.85 | s |
| 6 | 133.9 | 8.45 | dd (1, 7) |
| 4 | 138.6 | 9.24 | d (1) |
| 7a | 141.6 | | |
| COOH'$^c$ | 175.3 | | |
| COOH'$^c$ | 175.4 | | |

$^{a-c}$Assignments with the same C# may be interchanged. For example, 3'$^a$ and 3"$^a$ can be interchanged.
*Not assigned

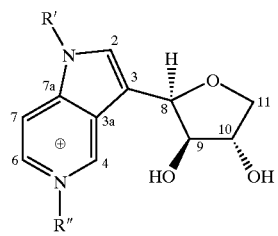

R', R" = CH$_2$(CH$_2$)$_2$COOH

Compound 3
  Fluorescent spectrum: EXmax=324 nm, EMmax=453 nm
  SIMS: m/z 421
  NMR spectrum: shown in Table 3

TABLE 3

NMR SPECTRUM for COMPOUND 3

(MeOH-d4)

| C# | $^{13}$C(ppm) | $^{1}$H(ppm) | (Hz) |
|---|---|---|---|
| 3'$^a$ | 25.3 | * | m |
| 3"$^a$ | 27.1 | * | m |
| 2'$^b$ | 30.8 | * | m |
| 2"$^b$ | 31.1 | * | m |
| 4' | 46.1 | 4.43 | t (7) |
| 4" | 55.2 | 4.59/4.80 | m, m |
| 4 | 70.6 | 5.20 | dd (2, 5) |
| 11a | 70.9 | 3.76 | dd (8, 8) |
| 11b | 70.9 | 4.14 | dd (8, 8) |
| 10 | 71.8 | 4.70 | ddd (5, 8, 8) |
| 3 | 75.9 | 5.26 | d (2) |
| 6 | 90.9 | 6.92 | s |
| 9 | 108.1 | 8.08 | d (7) |

TABLE 3-continued

NMR SPECTRUM for COMPOUND 3

(MeOH-d4)

| C# | $^{13}$C(ppm) | $^{1}$H(ppm) | (Hz) |
|---|---|---|---|
| 2a | 115.1 | | |
| 9b | 121.3 | | |
| 8 | 135.6 | 8.47 | d (7) |
| 2 | 136.8 | 7.96 | s |
| 9a | 141.8 | | |
| 6a | 150.1 | | |
| COOH'$^c$ | 175.6 | | |
| COOH"$^c$ | 176.0 | | |

$^{a-c}$Assignments with the same C# may be interchanged. For example, 3'$^a$ and 3"$^a$ can be interchanged.
*Not assigned

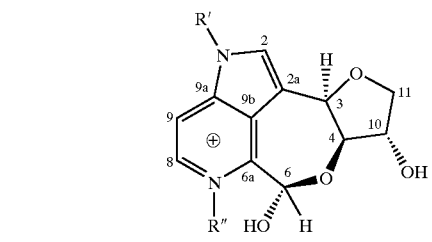

R', R" = CH$_2$(CH$_2$)$_2$COOH

Compound 4
  Fluorescent spectrum: EXmax=325 nm, EMmax=440 nm
  SIMS: m/z 609
  NMR spectrum: shown in Table 4

(MeOH-d4)

| C# | $^{13}$C(ppm) | $^{1}$H(ppm) | (Hz) |
|---|---|---|---|
| 4' | 48.5 | 4.37 | t (6) |
| 4" | 57.6 | 4.0–4.1 | m |
| 11a | 64.6 | 3.71 | dd (7, 12) |
| 11b | 64.3 | 3.97 | dd (3, 12) |
| 3 | 66.6 | 5.46 | s |
| 10 | 71.6 | 3.98 | m |
| 4 | 74.0 | 4.55 | d (9) |
| 6 | 93.0 | 6.77 | s |
| 9 | 110.0 | 7.97 | d (7) |
| 2a | 120.2 | | |
| 9b | 122.7 | | |
| 8 | 137.6 | 8.35 | d (7) |
| 2 | 137.9 | 7.95 | s |
| 9a | 143.8 | | |
| 6a | 149.5 | | |

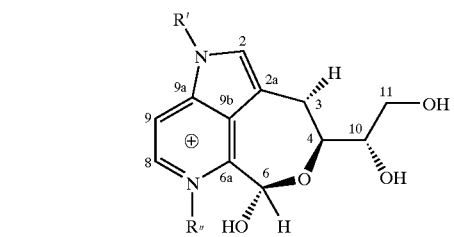

R', R" = CH$_2$(CH$_2$)$_3$CH(NHAc)COOH

Compound 5
Fluorescent spectrum: EXmax=324 nm, EMmax=453 nm
SIMS: m/z 591
NMR spectrum: shown in Table 5

| | (MeOH-d4) | | |
|---|---|---|---|
| C# | $^{13}$C(ppm) | $^1$H(ppm) | (Hz) |
| 4' | 48.5 | 4.37 | t (6) |
| 4" | 57.1 | 4.63 | m |
| 11a | 72.1 | 3.75 | dd (8, 8) |
| 11b | 72.1 | 4.17 | dd (8, 13) |
| 3 | 77.8 | 5.35 | d (1) |
| 10 | 72.9 | 4.85 | ddd (5, 8, 18) |
| 4 | 72.4 | 5.22 | d (1, 5) |
| 6 | 92.6 | 6.89 | s |
| 9 | 110.2 | 7.98 | d (7) |
| 2a | 120.2 | | |
| 9b | 123.0 | | |
| 8 | 137.6 | 8.39 | d (7) |
| 2 | 139.3 | 7.96 | s |
| 9a | 143.7 | | |
| 6a | 149.7 | | |

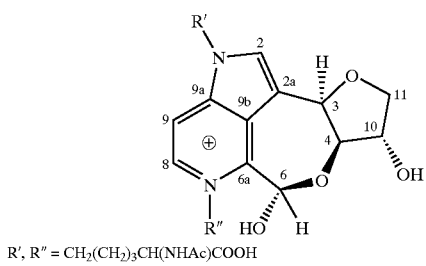

R', R" = CH$_2$(CH$_2$)$_3$CH(NHAc)COOH

EXAMPLE 5

The antibody against the pyrrolopyridinium derivatives of the present invention was prepared by a conventional method, i.e., a pyrrolopyridinium derivative of the present invention was combined with keyhole lympet hemocyanin and was administered to immunize a rabbit. The resulting antibody significantly reacted with various glycated proteins prepared in vitro. However, it did not react with normal proteins which were not glycated. Additionally, it has been clear that the antibody reacts with extracts of human lens and that the reaction increases commensurate with aging.

As discussed above, several candidates as Advanced Glycation Endproduct (AGE) have been shown and related studies are continuing. One of the candidates, a novel pyridinium derivative, was disclosed in the Laid-Open Japanese Patent Publication Hei-07/73057 and corresponding U.S. Pat. No. 5,338,850. The publication showed that the excitation wavelengths of the pyridinium derivatives are from 370 nm to 380 nm. On the other hand, the substances of the present invention have different fluorescent characteristics from that of known AGE. Since the excitation wavelengths of the substances of this invention are about 325 nm, the instant substances cannot be detected by fluorescent analysis using the said excitation wavelengths as reported above. The oxidation reaction is not needed for the production of said pyridinium derivatives. However, the substances of the present invention may be produced by both reactions of glycation and oxidation from consideration of the characteristic structure. Therefore, the instant substances are highly focused as a novel candidate for AGE.

As mentioned above, since many studies clarified that diabetic patients are kept under a higher oxygen-stressed condition than normal or non-diabetic persons, the crosslinked substances produced by both reactions of glycation and oxidation in the present invention are highly useful as a new indicator to diagnose diabetic complications and aging.

The pyrrolopyridinium derivatives of the present invention provide not only a novel AGE having an entirely new structural skeleton different from the conventional AGE, but is also thought because of its characteristic structure to be a cross-linked substance produced by both a glycation reaction and an oxidation reaction. In addition, it has a novel and unobvious hemiacetal structure showing a reactivity that is noteworthy as a new AGE. As mentioned already, various studies have clarified that, when compared with healthy people, diabetic patients and dialyzed patients are under a high oxygen stress and that cross-linked substances like the pyrrolopyridinium derivatives of the present invention that are produced by a glycation reaction and by an oxidation reaction are highly useful as new indexing compounds for the onset/progress of diabetic complications, dialytic complications and aging.

Accordingly, it is possible, using the pyrrolopyridinium derivatives of the present invention as an index, to conduct a test for diabetes mellitus, diabetic complications such as diabetic nephropathy, diabetic arteriosclerosis, diabetic neurosis, diabetic cataract, diabetic retinopathy, etc., dialysis-related complications, Alzheimer's disease and aging, and diseases accompanied thereby. It is also possible to evaluate pharmaceutical effectiveness, etc. using the pyrrolopyridinium derivatives of the present invention as an index in test systems both in vitro and in vivo. Further, an antibody prepared using the pyrrolopyridinium derivatives of the present invention as a hapten can be used in the above-mentioned testing and pharmaceutical evaluation via immunochemical and immunohistochemical assay methods. As mentioned above, the pyrrolopyridinium derivatives of the present invention comprise a novel and unobvious substance having a new structural skeleton containing an intramolecular hemiacetal that is clearly different from the known AGE. When present in organism the pyrrolopyridinium derivatives of the present invention have a bioactivity unlike the conventional AGE, whereby said derivatives are very useful in the present technical field where a great variety of AGEs are in demand.

We claim:

1. A pyrrolopyridinium derivative represented by the formula (II) or (III), stereoisomers and enantiomers thereof, and pharmaceutically acceptable salts of the derivatives, stereoisomers and enantiomers:

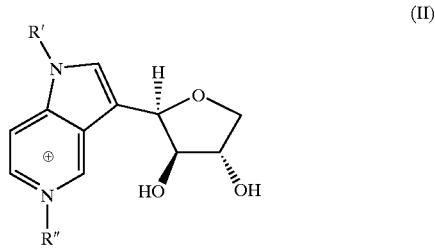

(II)

-continued

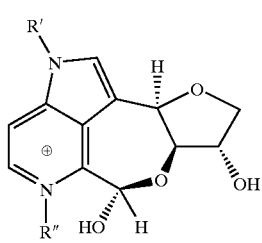
(III)

wherein R' and R" are the same or different and each of them is an alkyl group which may have: (1) at least one amino group and/or at least one carboxyl group, (2) at least one protected amino group, or (3) an amino group, a protected amino group, and a carboxyl group.

2. An antibody prepared from the pyrrolopyridinium derivative according to claim 1 as a hapten.

3. A pyrrolopyridinium derivative as claimed in claim 1 wherein R' and R" are the same.

4. A pyrrolopyridinium derivative as claimed in claim 1 which is of formula II or a pharmaceutically acceptable salt thereof.

5. A pyrrolopyridinium derivative as claimed in claim 1 wherein said alkyl group has 1–6 carbon atoms.

6. A method for the diagnosis of diabetes or diabetic complications comprising measuring the pyrrolopyridinium derivative according to claim 1 produced in an organism as an indicator of the degree of production or accumulation of Advanced Glycation Endproducts.

7. A method for the diagnosis of diabetes or diabetic complications comprising using the antibody according to claim 2 in an assay to evaluate the degree of production or accumulation of Advanced Glycation Endproducts produced in an organism.

8. A method for diagnosis according to claim 6 comprising measuring the pyrrolopyridinium derivative in at least one of a living tissue, an extract from living tissue, body fluid or urine.

9. A method for diagnosis according to claim 7 comprising measuring the Advanced Glycation Endproducts in at least one of a living tissue, an extract from living tissue, body fluid or urine.

10. A method for evaluating the effectiveness of pharmaceuticals as therapeutic agents for diabetes or diabetic complications comprising measuring the pyrrolopyridinium derivative according to claim 1 produced in an organism in the presence and absence of a test drug to evaluate the degree of production or accumulation of Advanced Glycation Endproducts.

11. A method for evaluating the effectiveness of pharmaceuticals as therapeutic agents for diabetes or diabetic complications comprising using the antibody according to claim 2 in the presence and absence of a test drug in an assay to evaluate the degree of production or accumulation of Advanced Glycation Endproducts produced in an organism.

12. A method for diagnosis according to claim 8, wherein said body fluid or urine is human blood, human plasma, human serum or human urine.

13. A method for diagnosis according to claim 9, wherein said body fluid or urine is human blood, human plasma, human serum or human urine.

14. A method for diagnosis according to claim 8, wherein the pyrrolopyridinium derivative is measured in human skin tissue or a human skin tissue extract.

15. A method for diagnosis according to claim 9, wherein the Advanced Glycation Endproducts are measured in human skin tissue or a human skin tissue extract.

16. A method for diagnosis as claimed in claim 6 wherein said pyrrolopyridinium derivative is of said formula II.

17. A method for diagnosis as claimed in claim 7 where said antibody is prepared from the pyrrolopyridinium derivative of said formula II.

18. A method for evaluating the effectiveness of pharmaceuticals as claimed in claim 10 where said pyrrolopyridinium derivative is of said formula II.

19. A method for evaluating the effectiveness of pharmaceuticals as claimed in claim 11 where said antibody is prepared from the pyrrolopyridinium derivative of said formula II.

20. An antibody according to claim 2 wherein said pyrrolopyridinium derivative is of said formula II.

21. A method for diagnosis according to claim 8 comprising measuring the pyrrolopyridinium derivative in vivo.

* * * * *